United States Patent [19]

Guglielmo et al.

[11] Patent Number: 4,827,024
[45] Date of Patent: May 2, 1989

[54] PROCESS FOR THE PREPARATION OF FLUOROXY-HALO-COMPOUNDS

[75] Inventors: Giorgio Guglielmo, Varese; Lino Conte, Padova; Filippo M. Carlini, Vicenza, all of Italy

[73] Assignee: Ausimont S.p.A., Milan, Italy

[21] Appl. No.: 837,133

[22] Filed: Mar. 7, 1986

[30] Foreign Application Priority Data

Mar. 11, 1985 [IT] Italy ................... 19847 A/85

[51] Int. Cl.$^4$ .................. C07C 69/63; C07C 69/96
[52] U.S. Cl. .................................................. 560/300
[58] Field of Search ............................................ 560/300

[56] References Cited

U.S. PATENT DOCUMENTS 2,689,254  9/1954  Cady et al. ........................ 560/300
3,442,927  5/1969  Thompson et al. ............... 560/300

OTHER PUBLICATIONS

J.A.C.S. 88:19, p. 4531, 1966 John K. Ruff et al.

*Primary Examiner*—Mary C. Lee
*Assistant Examiner*—Robert C. Whittenbaugh
*Attorney, Agent, or Firm*—Stevens, Davis, Miller & Mosher

[57] ABSTRACT

Preparation of fluoroxy-halo-compounds by direct reaction between fluorine and organic compounds having a molecular structure in which at least one oxygen atom is directly bound to a carbon atom in the carbonylic form, in the presence of a fluorination catalyst, in gaseous phase, at an absolute pressure of between 50 and 800 kPa and at a temperature between $-50°$ and $+100°$ C., under conditions of a continuous feeding of the reactants and a continuous removal of the reaction product.

12 Claims, No Drawings

PROCESS FOR THE PREPARATION OF FLUOROXY-HALO-COMPOUNDS

DESCRIPTION OF THE INVENTION

The present invention relates to a process for the preparation of fluoroxy-halo-compounds. More particularly, the present invention relates to a continuous process for the preparation of fluoroxy-halo-compounds of the formula:

$$(R)_nC(F)_m\text{—O—F} \qquad (I)$$

wherein

R is an alkyl or cycloalkyl radical containing from 1 to 12 carbon atoms, either partially or fully halogenated with bromine, chlorine and/or fluorine;

or R is a perfluoromonoether or perfluoropolyether radical containing from 1 to 12 carbon atoms;

n is an integer which is 1 or 2;

m is an integer equal to 3−n;

it being understood that the value n=2 comprises compounds in which C is part of a cyclic ring.

Fluoroxy-halo-compounds comprising the above indicated formula (I) are well known in the literature and described in U.S. Pat. No. 3,442,927; by John R. Ruff et al in *J.A.C.S.*, 88: 19, Oct. 5, 1966, pp. 4531–4532; and by Lustig et al in *J.A.C.S.*, 89: 12, June 7, 1967, pp. 2841–2843.

These compounds find useful applications as oxidizers, for example, in bleaching; as oxidizing agents in organic syntheses in various different applicational fields; as oxidizers in propellants; and as fluorinating agents.

The fluoroxy-halo-compounds have, so far, been considered to be of difficult production, mainly because of their great instability.

Due to the great instability of the products, the various processes proposed for their preparation heretofore are conducted under such drastic and limitative conditions as not to find practical industrial application.

In fact, operating according to the known processes, there are obtained very low yields (approximately 2%), or it is necessary to operate at very low reaction temperatures, such as in general at −78° C., or the reaction is not selective and byproducts are formed that subsequently have to be removed. At any rate, the known processes all operate in a discontinuous way and with very low quantities of reactant.

Thus, for instance, in *J.A.C.S.*, 88: 19, Oct. 5, 1966, on pp. 4531 and 4532, and in *J.A.C.S.*, 89: 12, June 7, 1967, on pp. 2841–2843, there is described the preparation of fluoroxyalkanes by the catalytic addition of fluorine on the double carbon/oxygen bond in a perfluorocarbonyl compound according to the scheme:

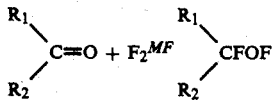

wherein $R_1$ and $R_2$ may be, independently from each other, fluorine or a perfluoroalkyl radical, while M is K, Na, Rb, or Cs.

The reaction is conducted in a discontinuous way, in small quantities, at a low temperature (−78° C.), at a reduced absolute pressure of 10 to 20 kPa, and over long times. Although the process allows one to obtain high yields (up to 98%), the quantity of fluoroxyalkanes obtainable does not exceed 10 mM (millimoles) per charge (batch).

U.S. Pat. No. 3,442,927 describes a process for the production of fluoroxy-compounds by direct reaction in a discontinuous way between fluorine with oxygen-containing compounds whose oxygen is directly bound to carbon, at temperatures between −100° and +50° C., in which process the desired products are isolated from the reaction mixture by fractional condensation using separators refrigerated with dry ice, liquid air, or ice-salt for the low-boiling products, and other suitable temperature conditions for the high-boiling liquids. The fluorine and the other gases are introduced into the reaction medium under a slight pressure and at a reaction time between 10 minutes and 12 hours.

The main drawbacks of this process consist in the lack of selectivity, in low yields, and in the necessity of carrying out the fractional separation of the products obtained, at a low temperature and under perfectly clean conditions in order to avoid explosive decompositions of the fluoroxy-compounds which, as is well known, are provoked by traces of pollutants.

Moreover, also in this process the reaction is conducted in a discontinuous way and on small quantities of product.

Thus, an object of the present invention is that of providing a process for the preparation of fluoroxy-compounds that will not display the above-mentioned drawbacks.

More particularly, an object of the present invention is that of providing an industrial process for the preparation of fluoroxy-compounds.

A further object of this invention is that of providing an industrial process that shall allow one to produce, in a selective way and with high yields, the desired fluoroxy compounds.

Still another object of the present invention is that of providing an industrial process that will allow one to obtain fluoroxy-compounds with a high productivity and high purity without requiring a subsequent isolation and/or manipulation, so as thereby to avoid the risks and limitations connected with great instability.

It has now, surprisingly, been found, according to the present invention, that these and other objects are obtained by carrying out a direct reaction between fluorine and organic compounds having a molecular structure in which at least one atom of oxygen is directly bound to a carbon atom in the carbonylic form, in the presence of a fluorination catalyst, in a gaseous phase, and under such conditions as to obtain the fluoroxy-halo-compound in the gaseous state, at an absolute pressure between 50 and 800 kPa, at a temperature greater than −50° C. and up to 150° C., under conditions of a continuous feeding of the reactants and a continuous removing of the reaction product, so that the mean dwell time (residence time) of the reactants in the reaction medium shall be less than 10 minutes, and under conditions of removal of the reaction heat, such as to maintain the temperature at values of not more than 150° C.

The gaseous mixture fed to the reaction zone may contain a diluent. The operating conditions for the reaction, including the possible dilution conditions, are chosen in such a way that the starting carbonyl compound and the obtained fluoroxy-halo-compound are both in the gaseous state.

According to a preferred embodiment of the present invention, the fluorination reaction is conducted by continuously passing the reactants in gaseous phase through a layer containing the catalyst and capable of insuring the attainment of the required heat exchange.

Compounds having a molecular structure in which at least one oxygen atom is directly linked to a carbon atom in a carbonylic form may be more specifically represented by the formula:

$$(R)_nC(X)_{m-1}O \qquad (II)$$

wherein O represents an oxygen atom directly linked to carbon, X represents fluorine or chlorine, while R, n and m have the same values and meanings as indicated above. When R contains H and/or Br, it is preferred to carry out the reaction at a temperature not higher than 50° C.

The compounds in which R represents a perfluoroalkyl radical having from 1 to 5 carbon atoms, or a perfluoromonoether or perfluoropolyether radical having from 1 to 5 carbon atoms, are preferred compounds in the process of the present invention.

Examples illustrating the starting compounds to be subjected to the fluorination process according to the present invention are: fluoride and chloride of trifluoroacetyl; fluoride and chloride of chloro-difluoro-acetyl; fluoride and chloride of trichloro-acetyl; fluoride and chloride of bromo-difluoroacetyl; fluoride and chloride of pentafluoro-propionyl; fluoride and chloride of heptafluoro-butyryl; hexafluoroacetone; perfluoroethoxy-difluoro-acetyl-fluoride; perfluoromethoxydifluoro-acetylfluoride; and mixtures thereof.

The reactants are continuously fed in, in gaseous phase, preferably under a slight pressure and in equimolar quantities, with flow rates for each reactant greater than $5 \cdot 10^{-6}$ mol/hr per gram of catalyst. Flow rates for each reactant between $10^{-4}$ and $10^{-1}$ mol/hr per gram of catalyst are preferred.

The reactants are preferably diluted with an inert gas in order to obtain concentrations between 5 and 70% by volume. As an inert gas, there may be used any gas or vapor that is nonreactive with the reactants and the reaction products, such as, for instance, nitrogen, argon, helium, tetrafluoromethane, dichlorotetrafluoroethane, pentafluorochloroethane, difluorodichloromethane, perfluorocyclobutane, etc.

As catalyst, there may be used any kind of known fluorination catalyst, particularly cesium fluoride, rubidium fluoride, potassoum fluoride, lithium fluoride or sodium fluoride, although cesium fluoride is preferred.

In order to remove the reaction heat and achieve the required heat exchange, the process of the present invention is carried out either in the presence of a metallic material essentially inert towards fluorine, or in a metal reactor having such a geometric configuration as to insure the required heat exchange.

Among the metallic materials suited for the purpose are preferably copper and its alloys, such as brass and Monel, although other materials may also be used. The catalyst may be mixed with the metallic material, said material being in the form of chips (shavings), Raschig rings, or similar filling bodies, or it may be supported on said metallic material which is in one of the abovesaid forms. It is also possible to use the catalyst both mixed with the metallic material and supported on it.

According to a preferred embodiment of the present invention, the catalyst is mixed with the metal material and/or supported on it, said metal material being in the form of shavings (chips), Raschig rings or similar filling bodies, and the reactants, in gaseous phase and diluted in an inert gas, are continuously passed through a fixed layer of the metallic material catalyst, with such a flow speed as to maintain the dwell time in the reactor below 10 minutes, keeping the reaction temperature at a value between $-20°$ and $100°$ C., but preferably between $20°$ and $60°$ C., while the absolute pressure is maintained between 100 and 200 kPa.

In order to regulate or control the reaction temperature, any suitable known means may be used, for instance, a thermostatic bath. The gaseous mixture that goes into the reaction zone must be well-purified from HF, $H_2O$, and from the acid or dialcohol that can form by hydrolysis of the starting carbonylic compound. More precisely, the inert gas must be purified from $H_2O$, the $F_2$ from HF, and the starting carbonylic compound from HF and from the possible acid or dialcohol.

The process of the present invention allows one to obtain full conversion of the reactants with stoichiometric yields in pure fluoroxy-compound, which does not need any successive operations for its isolation or purification.

The fluoroxy compounds obtained according to the present invention find useful applications in condensation and/or fluorination reactions of the most varied organic substrates (compounds), such as olefins, unsaturated compounds, organic compounds having hydrogen or functional groups that can be substituted with fluorine, etc., or they may be decomposed with the formation of $COF_2$ and of the corresponding halogeno-compound.

In order still better to understand this invention, and for its practical applications, the following will be given a series of illustrative, but not limiting, examples.

EXAMPLE 1

Into a brass reactor having a diameter of 50 mm and a useful holding capacity of 500 cc, completely filled with copper chips (shavings) intermingled with 300 g of CsF, dried at 250° C. in a flow of nitrogen during 4 hours, milled and screened in a dry box in order to obtain a granulometry between 250 and 500 microns, there were fed in continuously a mixture of $N_2/F_2/CF_3COF$ purified from HF, $H_2O$ and the acid or dialcohol that can form by hydrolysis of the starting carbonylic compound, in a molar ratio equal to 3.75/1/1, at a global or overall flow rate of 23 Nl/hr ($6 \cdot 10^{-4}$ mol/hr per gram of catalyst for each reactant), and at an absolute pressure of 110 kPa. The temperature inside the reactor was kept at $-10°$ C. by means of external cooling.

The gaseous mixture flowing out of the reactor, after analysis by IR spectrophotometry and iodometry, proved to consist of $N_2/CF_3CF_2OF$ in a molar ratio of 3.75/1, with a 100% conversion and a 100% yield in perfluoro-ethoxy-fluoride.

After 400 hours of operation, the conversion of the reactants and the yield remained unvaried.

On increasing the temperature inside the reactor to $+20°$ C., or increasing the absolute pressure to 500 kPa, the conversions and the yields remained unvaried at the value of 100%.

EXAMPLE 2

Into the reactor described in Example 1, there was continuously fed in a gaseous mixture consisting of $N_2/F_2/CF_3COF$, purified as indicated above, in a molar ratio of 1/1/1, at a global flow rate of 12 Nl /hr ($6 \cdot 10^{-4}$ mol/hr per gram of catalyst for each reactant), and at an absolute pressure of 110 kPa. The temperature inside the reactor was maintained at +20° C. by means of a thermostatically-controlled bath. The gaseous mixture flowing out of the reactor, analyzed by means of IR spectrophotometry and iodometry, proved to consist of $N_2/CF_3CF_2OF$ in a molar ratio of 1/1, with 100% conversion and yield.

Even after several weeks of operation, no variations in the conversion and/or yield could be noticed.

EXAMPLE 3

Into the same reactor as that of Example 1, there was continuously fed in a gaseous mixture of $N_2/F_2/CClF_2COF$, purified as indicated above, in a molar ratio of 3.75/1/1, at a total flow rate of 23 Nl/hr ($6 \cdot 10^{-4}$ mol/hr per gram of catalyst for each reactant), and at an absolute pressure of 110 kPa.

The temperature inside the reactor was maintained at 20° C. The gaseous mixture flowing out of the reactor, analyzed by means of IR spectrophotometry and iodometry, proved to consist of $N_2$ and $CClF_2—CF_2OF$ in a molar ratio of 3.75/1, with a 100% conversion and a 100% yield in 2-chloro-tetrafluoro-ethoxyfluoride.

The yield and the conversion remained unvaried after several weeks.

EXAMPLE 4

Into an AISI 316 reactor of 25 mm diameter and of 500 cc holding capacity, completely filled with Raschig copper rings of 4 mm size, intermingled with 300 g of CsF treated as indicated in Example 1, was fed in continuously a gaseous mixture of $N_2/F_2/CF_3COF$, purified as indicated above, in a molar ratio of 30/2/1, and at a total flow rate of 16.5 Nl/hr ($7.4 \cdot 10^{-5}$ mol/hr of $CF_3COF$ per gram of catalyst and $14.9 \cdot 10^{-5}$ mol/hr of fluorine per gram of catalyst), and at an absolute pressure of 110 kPa.

The temperature inside the reactor was kept at 135° C. by means of a thermostatic bath. The outflowing gases were analyzed by IR spectrophotometry and iodometry, and they proved to consist of $N_2$ and $CF_3CF_2OF$ with a complete conversion of $CF_3COF$ into $CF_3CF_2OF$.

EXAMPLE 5

Into the reactor described in Example 4 was continuously fed in a gaseous mixture consisting of $C_2ClF_5/F_2/CF_3COF$, purified as indicated above, in a molar ratio of 1/1/1, at a total flow rate of 45 Nl/hr ($2.2 \cdot 10^{-3}$ mol/hr per gram of catalyst per each reactant), and at an absolute pressure of 110 kPa. The temperature in the reactor was kept at 20° C. by means of external cooling.

The outflowing gaseous mixture, analyzed by means of IR spectrophotometry and iodometry, proved to consist of $C_2ClF_5/CF_3CF_2OF$ in a molar ratio equal to 1/1, with a 100% conversion and a 100% yield in pentafluoro-ethoxy-fluoride.

EXAMPLE 6

Into the same reactor as that of Example 1, there was continuously fed in a gaseous mixture of $N_2/F_2/CF_3COCl$, purified as indicated above, in a molar ratio of 3.75/1.5/1, at a global flow rate of 25 Nl/hr ($9 \cdot 10^{-4}$ mol/hr of fluorine per gram of catalyst and $6 \cdot 10^{-4}$ mol/hr of $CF_3COCl$ per gram of catalyst), and at an absolute pressure of 110 kPa.

The temperature inside the reactor was maintained at 30° C. by an external cooling. The outflowing gaseous mixture, analyzed by means of IR spectrophotometry and iodometry and titration of chlorides, proved to consist of $N_2/CF_3CF_2OF/Cl_2$ in a molar ratio of 7.5/2/1, with a 100% conversion and a 100% yield of penta-fluoro-ethoxy-fluoride.

EXAMPLE 7

Into the reactor of Example 1, there was continuously fed in a gaseous mixture of $N_2/F_2/(CF_3)_2CO$, purified as indicated above, in a molar ratio of 3.75/1/1, at a global flow rate of 23 Nl/hr ($6 \cdot 10^{-4}$ mol/hr per gram of catalyst for each reactant), and at an absolute pressure of 110 kPa. The temperature inside the reactor was maintained at 20° C. by external cooling.

The outflowing gaseous mixture, analyzed by IR spectrophotometry and iodometry, proved to consist of $N_2/(CF_3)_2—CF—O—F$ in a molar ratio of 3.75/1, with a 100% conversion and yield.

EXAMPLE 8

This is operated as in Example 7, feeding a gaseous mixture of $N_2/F_2/CF_3—CF_2—COF$, purified as indicated above. There is obtained $CF_3—CF_2—CF_2—OF$ with conversion and yield of 100%.

EXAMPLE 9

This is operated as in Example 7, feeding a gaseous mixture of

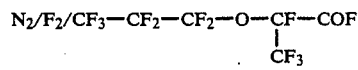

purified as indicated above. There is obtained

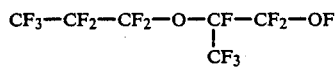

with conversion and yield of 100%.

What is claimed is:

1. A process for the preparation of fluoroxy halo compounds of the formula:

wherein

R is an alkyl radical having from 1 to 12 carbon atoms, either partially or fully halogenated with bromine, chlorine and/or fluorine, or R is a perfluoromonoether radical or a perfluoropolyether radical having from 1 to 12 carbon atoms;

n is an integer which is 1 or 2; and m is an integer equal to $3-n$;

in which an acyl halide or a ketone of the formula

wherein

O represents an oxygen atom directly linked to the carbon atom in the carboxylic form;

X represents fluorine or chlorine; and

R, m and n having the above meanings, is reacted with fluorine in the presence of a fluorination catalyst selected from the group consisting of cesium fluoride, rubidium fluoride, potassium fluoride, lithium fluoride and sodium fluoride; the reaction being conducted in gaseous phase, and under such conditions as to obtain the fluoroxy halo compound in the gaseous state, at an absolute pressure between 50 and 800 kPa and at a temperature higher than $-50°$ C. and up to 100° C., under conditions of continuous feeding of the reactants and continuous removal of the reaction product, so that the dwell time of the reactants in the reaction medium is less than 10 minutes, and under conditions of removal of the reaction heat in order to maintain the temperature at values not exceeding 100° C.

2. A process according to claim 1, in which the fluorination catalyst is cesium fluoride.

3. A process according to claim 1, in which R represents a perfluoro alkyl radical having from 1 to 5 carbon atoms.

4. A process according to claim 1, in which R represents a perfluoromonoether or perfluoropolyether radical having from 1 to 5 carbon atoms.

5. A process according to claim 1, 2, 3 or 4, in which the reaction between the fluorine and the acyl halide or a ketone is conducted by means of a continuous passage of the reactants in gaseous phase through a fixed bed containing the catalyst and capable of insuring the required thermal exchange.

6. A process according to claim 1, 2, 3 or 4, in which the reaction is conducted in the presence of a metallic material essentially inert towards fluorine.

7. A process according to claim 6, in which the catalyst is intermingled with the said metallic material, said metallic material being in the form of chips (shavings), Rashig rings or similar filling bodies and/or is supported on said metallic material.

8. A process according to claim 6, in which the metallic material is copper or alloys thereof, such as brass or Monel.

9. A process according to claim 1, 2, 3 or 4, in which each reactant is fed in at a flow rate greater than $5 \cdot 10^{-6}$ mol/hr per gram of catalyst.

10. A process according to claim 9, in which the flow rate for each reactant is between $10^{-4}$ and $10^{-1}$ mol/hr per gram of catalyst.

11. A process according to claim 1, 2, 3 or 4, in which the catalyst is intermingled with a metallic material essentially inert towards fluorine, in the form of chips, Rashig rings or similar filling bodies and/or supported on said metallic material, and the reactants, in gaseous phase and diluted in an inert gas, are continuously passed through a fixed layer of metallic material/catalyst at a speed corresponding to a dwell time in the reactor below 10 minutes, while maintaining the reaction temperature between $-20°$ and $+100°$ C., while the absolute pressure is between 100 and 200 kPa.

12. A process according to claim 11, in which the reaction temperature is maintained between 20° and 60° C.

* * * * *